United States Patent [19]

Kelman

[11] Patent Number: 4,791,924

[45] Date of Patent: Dec. 20, 1988

[54] LENS FORCEPS AND METHOD OF USE THEREOF

[76] Inventor: Charles D. Kelman, 269 Grand Central Parkway, Floral Park, N.Y. 11005

[21] Appl. No.: 57,276

[22] Filed: Jun. 2, 1987

[51] Int. Cl.⁴ .............................................. A61B 17/00
[52] U.S. Cl. ................................................ 128/303 R
[58] Field of Search ................... 128/321, 354, 303 R

[56] References Cited

U.S. PATENT DOCUMENTS

4,706,666 11/1987 Sheets ............................ 128/303 R

Primary Examiner—Michael H. Thaler
Attorney, Agent, or Firm—Henry Sternberg; Bert J. Lewen

[57] ABSTRACT

Lens forceps and method of use thereof for extractive removal from the interior of an eye through a corneal incision of a surgically severed segmental lens fragment, the forceps contemplating a manually manipulatable eye lens size clamp of two relatively longitudinally movable parts, including a scoop part having a handle provided with a crescent shaped scoop extending therefrom and defining an upwardly open receiving trough of conforming size and shape to the profile of such a fragment for receiving the fragment therein, and a cover part having a handle provided with a cover extending therefrom, the parts being arranged for manually controlled relative longitudinal movement therebetween and, in one position of such movement, for manually controlled removable stationary engagement of the handles and corresponding positioning of the cover over the scoop to form therewith a cage to retain the fragment for permitting removal thereof from the eye through the corneal incision.

12 Claims, 2 Drawing Sheets

LENS FORCEPS AND METHOD OF USE THEREOF

FIELD AND BACKGROUND OF THE INVENTION

The present invention relates to lens forceps for extractive removal from the interior of an eye through a corneal incision of a surgically severed individual segmental lens portion or fragment, and more particularly to a lens forceps assembly formed as a manually manipulatable eye lens size clamp and a method of use thereof for such extractive removal.

U.S. Pat. No. 2,865,099 to Blackwood shows a surgical scissor instrument, having a crescent shaped member pivoted to a counterpart jamming member, and usable externally for cutting sutures sewn through the epidermis of a patient, and removing the cut strands, all in one operation. This gross instrument is inappropriate for use in sensitive, confined areas such as the interior of a human eye.

A recent innovation in ophthalmic surgery, such as in the treatment of a cataracted lens of a human eye, involves cutting the natural lens within the eye into severed portions or fragments, and removing the individual fragments through a small incision in the cornea.

Specifically, the natural lens may be cut within the eye, while still in the posterior chamber, by means of a laser or a Phaco-Emulsifier (i.e. in a straight line), or the lens may be displaced by the surgeon into the anterior chamber of the eye, and there be cut with tee aid of a surgical instrument such as a loop-snare (see U.S. Pat. No. 4,588,611 to Kelman), specially designed scissor, or similar instrument, inserted into the anterior chamber through a corneal incision. In each case, the lens is cut into two or more fragments, e.g. of segmental strip shape.

Obviously, the linear extent of the corneal incision needed to remove these cut lens strip fragments will be only a fraction of the incision length needed to remove the whole lens in one piece. Previously, when the lens as a whole was to be extracted, the surgeon could merely press the eyeball to squeeze the lens out through an appropriately large incision. In such a procedure, since the natural lens substantially fills the anterior chamber of the eye, pressure on the eyeball readily expels the lens. However, with the lens cut into several pieces, this removal method is no longer applicable.

It will be appreciated that an eye lens is of generally negligible axial thickness but has a diameter of about 10 mm, such that any corneal incision will accommodate the negligible lens thickness, whereas the incision length will depend on the particular procedure involved.

Thus, an incision length slightly exceeding 10 mm is needed to remove the whole uncut lens. On the other hand, a incision length of at most about 6 mm is needed when using a loop-snare as earlier described, e.g. to cut the lens into two half circle shaped strips, each having about a 10 mm maximum chordal width dimension (strip length), here corresponding to the diameter length, and about a 5 mm maximum arc height (strip width), here corresponding to the radial length increment along a perpendicular line, here the radius, from the midpoint (here the lens center) of the chord of cutting to the tangent point on the cut lens circumference in a line parallel to the chord.

Clearly, by utilizing an eye insertable surgical lens cutting instrument of optimal minimum cross sectional width and height dimensions, such as a loop-snare, ay increase in the incision size beyond that needed for such instrument will only be due to increased corresponding cross sectional width and height dimensions of any mechanical means employed for extractive removal of the severed lens fragments from the eye interior and/or to the cross sectional chordal width (strip length) and arc height (strip width) dimensions, as above defined, of the cut lens fragments themselves.

Understandably, any such incision in the cornea should be as small as possible to minimize injury to the eye. Accordingly, the providing of a surgical instrument and method of using the same for facilitating removal of the individual lens segmental fragments from the eye interior in connection with optimal minimum size corneal incisions otherwise needed for carrying out the above described lens cutting procedures would be highly advantageous.

SUMMARY OF THE INVENTION

It is among the objects and advantages of the present invention to overcome the drawbacks and deficiencies of the prior art, and to provide a surgical instrument of essentially only two relatively movable parts, and a method of using the instrument as lens forceps for extractive removal from the interior of an eye through an optimal minimum linear size corneal incision of a surgically severed individual segmental lens portion or fragment.

It is among the additional objects and advantages of the present invention to provide a lens forceps assembly and method of using the same as stated, in which the forceps serve as a manually manipulatable eye lens size longitudinal clamp of minimum girth or cross section, especially as to its composite cross sectional linear height dimension, to enable the same to be efficiently inserted into the eye via a like minimum size incision in the cornea, operated in that inserted condition for retrieving captively the severed lens portion to be extracted, and thereafter removed, with minimum trauma to the patient.

It is among the further objects and advantages of the present invention to provide a lens forceps assembly of the stated type, which is comparatively simple and economical in construction, readily fabricated from surgical type metal material such as stainless steel, inert plastic material, etc., manually manipulatable with ease for precise operation, and generally durable and unfailing in use.

According to one feature of the present invention, lens forceps are provided for extractive removal from the interior of an eye through a corneal incision of a surgically severed individual segmental lens portion or fragment, the lens forceps comprising a manually manipulatable eye lens size clamp of two relatively longitudinally movable parts, including a longitudinal scoop clamp part and a longitudinal cover clamp part.

The scoop clamp part has a scoop handle provided with a generally crescent shaped longitudinal scoop forwardly extending from the scoop handle and defining an upwardly open receiving trough of conforming size and shape to the corresponding perimetric profile of such a segmental lens portion for receiving the lens portion therein, and the cover clamp part has an overlay handle provided with a longitudinal scoop cover forwardly extending from the overlay handle.

These two clamp parts are cooperatively arranged for manually controlled relative longitudinal movement therebetween, e.g. from a cover clamp part rearwardly retracted position to a cover clamp part extended position, and in one position of such movement, e.g. said extended position, for manually controlled removable coactive stationary engagement of the overlay handle with the scoop handle and corresponding positioning of the scoop cover in overlying covering relation with the scoop and forming therewith a confining cage for clamped captive retention of the lens portion therein for permitting removal thereof from the eye through the corneal incision.

Desirably, releasable interlocking means are provided on the two clamp parts for maintaining the parts in interlocked stationary engagement and cage forming relation when they are in said on position. The interlocking means may include cooperating interlocking elements located correspondingly on the scoop handle and overlay handle, such as in the form of protrusions on one such handle and protrusion receiving locking recesses on the other such handle.

Preferably, the scoop trough is generally V-shaped in cross sectional profile.

Guide means are favorably provided for maintaining the two parts in generally fixed transverse positional relation to each other while permitting relative longitudinal movement therebetween.

In one specific form, the scoop trough has upwardly directed lateral side walls and the scoop cover has lateral side portions arranged for spaced overlying registry with the trough side walls when the parts are in said one position. In this case, the guide means may include downwardly depending lateral skirts provided on the scoop cover lateral side portions in facing spaced relation to the trough side walls when the parts are in said one position, and arranged for guidingly embracing the coextensive adjacent portions of the scoop handle during a corresponding portion of such relative longitudinal movement, e.g. between the retracted and extended positions of the cover clamp part.

More particularly, the scoop favorably has a longitudinal dimension preferably generally corresponding to at most the diameter of an eye lens, and a depth dimension from the level of the scoop handle to the level of the lowermost portion of the scoop trough of preferably less than the corresponding radius of the eye lens, whereby to enable the assembly to be inserted operatively through a corresponding optimal minimum linear size corneal incision.

In turn, the scoop cover skirts and trough side walls are analogously sized to provide, when the two clamp parts are in said one position, a selective gap therebetween of a distance at most equal to preferably about one fourth of the corresponding longitudinal dimension of the scoop.

According to another feature of the present invention, a method of using the lens forceps is provided, for extractive removal from the interior of an eye through a corneal incision of a surgically severed individual segmental lens portion or fragment located in the anterior chamber of the eye.

The method comprises inserting the scoop of the scoop clamp part through such incision into the anterior chamber of the eye and manipulating the inserted scoop sufficiently for spatially positioning such segmental lens portion therein with the corresponding peripheral edge portion of the lens portion in receiving disposition along the scoop trough, and then inserting the scoop cover of the cover clamp part through the incision sufficiently for manually controlled coactive stationary engagement of the overlay handle with the scoop handle exterior to the eye and corresponding positioning of the inserted scoop cover in overlying covering relation with the scoop for forming therewith a confining cage in the anterior chamber for clamped captive retention of the lens portion therein.

These two steps are followed by the final step of removing simultaneously the scoop and scoop cover through the corneal incision while maintaining the scoop cover in overlying covering relation with the scoop and the overlay handle in coactive stationary engagement with the scoop handle.

BRIEF DESCRIPTION OF THE DRAWINGS

Other and further objects and advantages of the present invention will become apparent from the within specification and accompanying drawings, in which:

FIG. 8 is a schematic view of the manner in which the lens forceps of the present invention are used for recovering a severed segmental lens portion from the anterior chamber of a human eye.

DESCRIPTION OF THE PREFERRED EMBODIMENTS

Referring to the drawings, and initially to FIGS. 1-5, a lens forceps assembly 1 according to one embodiment of the present invention is shown, which is usable for extractive removal from the interior of an eye through an optimal minimum linear size corneal incision of a surgically severed individual segmental lens portion or strip fragment. Assembly 1 comprises a manually manipulatable eye lens size clamp of two relatively longitudinally movable parts.

Figure 4:
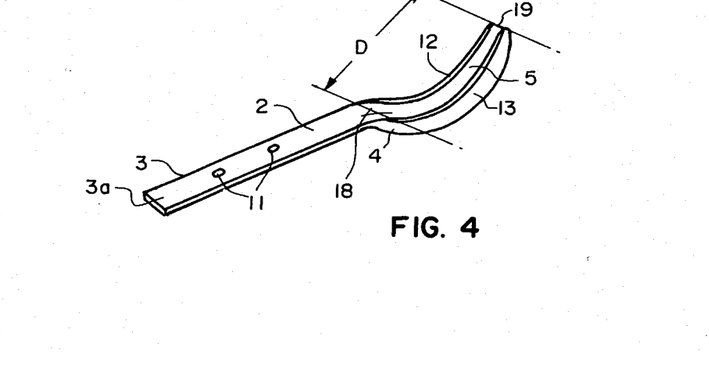
FIGS. 4 and 5 are corresponding schematic perspective views of the erect scoop clamp part and inverted cover clamp part, respectively, forming the lens forceps of FIG. 1.
Figure 6:
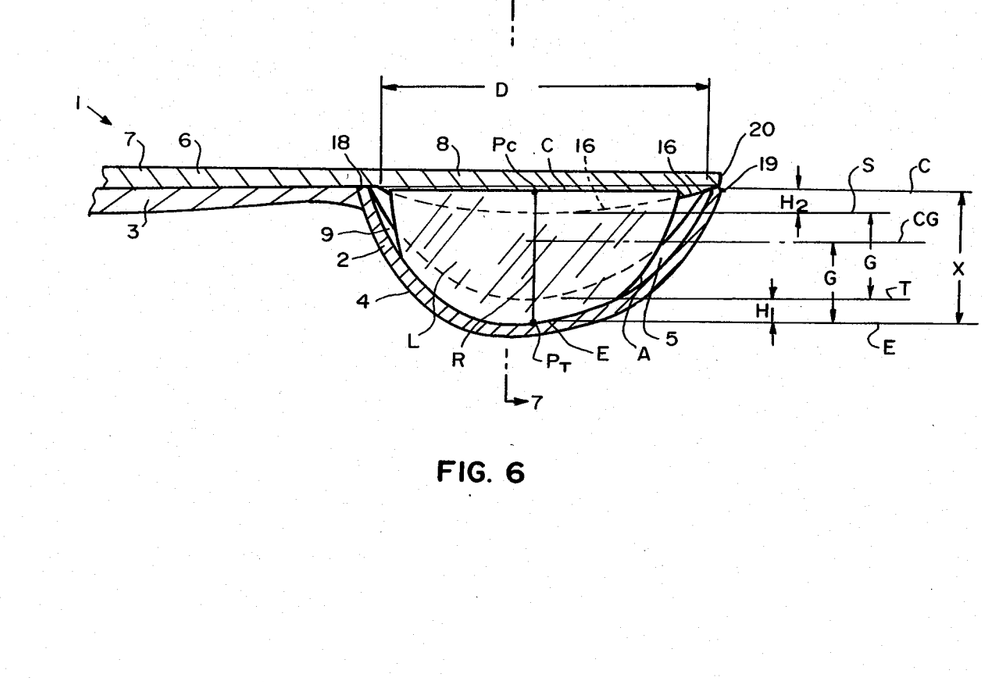
FIG. 6 is a schematic sectional side view of the lens forceps of FIG. 1, illustrating the positional disposition of a severed segmental lens portion recovered from the interior of the eye and captively retained in the cage formed by the clamp parts.
Figure 7:
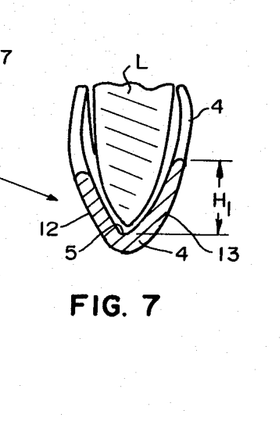
FIG. 7 is a schematic sectional view taken along the line 7—7 of FIG. 6.

One of these two parts is a longitudinal scoop clamp part 2, having a generally flat scoop handle 3 provided with a generally upwardly open crescent shaped or sickle shaped longitudinal curved scoop 4 forwardly extending from scoop handle 3 and defining an upwardly open receiving trough 5 of conforming size and shape to the corresponding perimetric profile of such a segmental lens portion or fragment L for receiving the fragment therein (see FIGS. 6 and 7).

Figure 5:
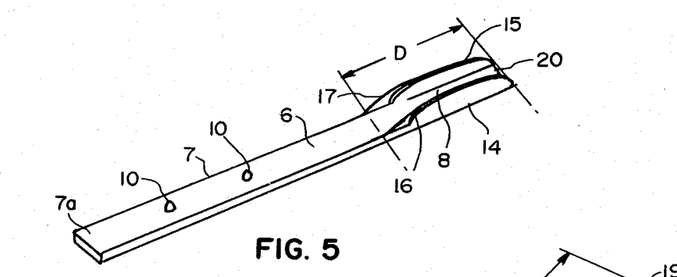

The other of these two parts is a longitudinal cover clamp part 6, having a generally flat overlay handle 7 provided with a longitudinal scoop cover 8 forwardly extending from overlay handle 7 in the form of a generally flat plate-like retainer.

Figure 1:
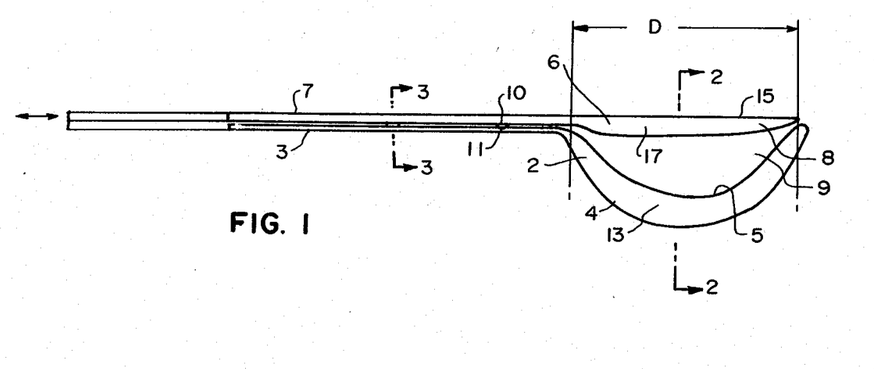
FIG. 1 is an exaggerated size schematic side view of the assembled parts of the lens forceps according to an embodiment of the present invention.

Clamp parts 2 and 6 are cooperatively arranged for manually controlled relative longitudinal movement therebetween and, in one position of such movement, as shown in FIG. 1, for manually controlled removable coactive stationary engagement of overlay handle 7 with scoop handle 3, i.e. along the common slidable coacting extent of the scoop handle upper slide surface 3a (FIG. 4) and overlay handle underside slide surface 7a (FIG. 5), and corresponding positioning of scoop cover 8 in overlying covering relation with scoop 4 and forming therewith a confining cage 9 for clamped captive retention of such a lens portion therein for permitting removal thereof from the eye through the corneal incision.

Thus, in effect, cover clamp part 6 is manually movable from a rearwardly retracted position, in which scoop cover 8 uncovers scoop 4 and embraces instead the adjacent coextensive longitudinal portion of scoop handle 3, to a forwardly extended position, in which scoop cover 8 overlies scoop 4 and trough 5 and overlay handle 7 is in more or less full registry with scoop handle 3 therebelow as shown in FIG. 1.

In this regard, releasable interlocking means are provided on clamp parts 2 and 6 for maintaining such parts in interlocked stationary engagement and cage forming relation, e.g. when cover clamp part 6 is in forwardly extended position. The interlocking means may be provided as cooperating interlocking elements located correspondingly on scoop handle 3 and overlay handle 7, here shown in the form of longitudinally spaced apart protrusion 10 on the underside surface 7a of overlay handle 7 and equally longitudinally spaced apart protrusion receiving locking recesses on the upper side surface 3a of scoop handle 3, arranged for registry and manually releasable interlocking stationary engagement with each other upon relative longitudinal movement of clamp parts 2 and 6 to bring such elements into proper coacting interlocking alignment.

Figure 8:
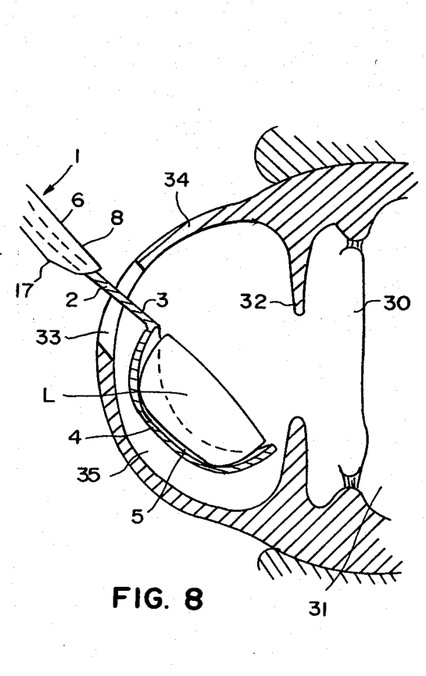

Preferably, protrusions 10 are provided in the form of relatively short upright pyramidal or conical bosses or like type generally pointed or angular apex male elements, and recesses are provided in the form of counterpart shallow inverted hollow pyramidal or conical recesses or like type inwardly generally pointed or angular apex female elements, so that the protrusions 10 will enter and leave the corresponding recesses 11 with minimum resistance in the longitudinal direction of relative travel of clamp parts 2 and 6 when no manual squeezing pressure is exerted transversely of the longitudinal direction, whereas once in interlocking engagement the coacting protrusions 10 and recesses 11 will efficiently resist all relative movement between clamp parts 2 and 6 when they are subjected to such manual squeezing pressure, e.g. exerted in the vicinity of the rearwardly located longitudinally coaligned handles 8 and 7 (see FIGS. 1 and 8).

Of course, as the artisan will appreciate, these releasable interlocking elements may be reversed, such that the protrusions 10 may be located on the upper side surface 3a of scoop handle 3, and the protrusion receiving locking recesses 11 may be provided on the underside surface 7a of overlay handle 7. Also, as contemplated herein, equivalent means may be employed instead to accomplish the releasable interlocking of clamp parts 2 and 6, upon relative longitudinal movement between these two parts to bring the particular interlocking elements into and out of registry for such engagement, in dependence upon the application of manual squeezing pressure such as to the handles 3 and 7, once the interlocking elements have been brought into coacting registry.

Figure 2:
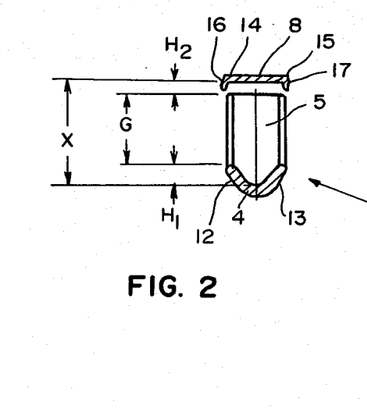
FIGS. 2 and 8 are schematic sectional views, taken along the lines 2—2 and 3—3, respectively, of the lens forceps of FIG. 1.
Figure 3:
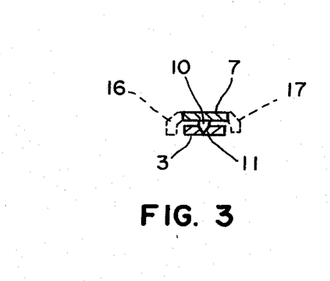

Desirably, as may be seen from FIGS. 2 and 7, scoop trough 5 is generally V-shaped in cross sectional profile. In any case, trough 5 contains upwardly directed lateral side walls 12,13, and scoop cover 8 contains lateral side portions 14,15, arranged for spaced overlying registry with the corresponding side walls 12,13 when cover clamp part 6 is in extended position, and provided with downwardly depending lateral skirts 16,17 for arrangement in facing spaced relation to the trough side walls 12,18, as shown in FIG. 2.

Lateral skirts 16,17 serve as a convenient form of guide means for maintaining clamp parts 2 and 6 in generally fixed transverse positional relation to each other, preventing yaw while permitting relative longitudinal movement between such clamp parts 2 and 6. Specifically, as shown in phantom in FIG. 3, lateral skirts 16,17 are arranged on scoop cover 8 of overlay handle 7 for guidingly embracing the adjacent portions, including the parallel side edges, of scoop handle 3 during relative longitudinal travel of clamp parts 2 and 6, e.g. during forward movement of clamp part 6 to extended position.

In accordance with a particular feature herein, scoop 4 has a longitudinal dimension D (see FIGS. 1, 4 and 6) preferably generally corresponding to at most the diameter of an eye lens, e.g. about 10 mm, and especially a dimension of at most about 6 mm, for a corresponding scoop radius of at most about 5 mm, and especially at most about 3 mm. The depth dimension X (see FIGS. 2 and 6) from the level of scoop handle 3 to the level of the lowermost portion of trough 5 is preferably less than the corresponding radius of the eye lens, e.g. less than about 5 mm, such as roughly about 3 mm.

In particular, the scoop depth dimension X is preferably about one third to one fourth of the scoop longitudinal dimension D, for accommodating lens strip fragments made by cutting a given lens correspondingly into three or four more or less equal width strip segments or partial segments per the aforedescribed procedure. In this way, the cross sectional height dimension of the assembly will be kept to an efficient minimum for insertion and withdrawal into the anterior chamber of the eye through a like minimum length corneal incision (see FIG. 2).

Also, scoop cover skirts 16,17 and trough side walls 12,13 are sized to provide a selective gap G therebetween (see FIGS. 2 and 6) of a distance preferably at most equal to about one fourth of the corresponding longitudinal dimension D of scoop 4, e.g. with trough side walls 12,18 each being about 1 mm in length, i.e. in composite height $H_1$ in the direction toward scoop cover skirts 16,17, and with such skirts 16,17 having an appropriate analogously short linear dimension, i.e. composite height $H_2$ in the facing direction, yet sufficient to embrace the thickness of scoop handle 3 see FIG. 8).

Of course, the transverse width dimension of the assembly, and especially of the forwardly located insertion portions, will understandably be only slightly larger than the corresponding axial thickness of the natural eye lens itself.

As may be seen from FIG. 6, the medial upper end 18 and distal upper end or tip 19 of scoop 4 are located at an upper level in a common transitional plane passing through the scoop handle upper side surface 3a and the overlay handle underside surface 7a when the protrusions 10 and recesses 11 are in interlocking arrangement, such that the thereby cantilevered distal end or tip 20 of scoop cover 8 seats downwardly against the distal upper end or tip 19 of scoop 4 acting as supporting anvil therefor. Such construction results in a sturdy interconnection of clamp parts 2 and 6 when cover clamp part 6 is in extended position for providing the captive cage 9, which is facilitated by the coaction between the interlocking elements 10 and 11, and which is easily and efficiently controlled by simple finger pressure of the surgeon manually manipulating the two clamp parts via handles 3 and 7.

Furthermore, it will be appreciated that the very nature of the angularly offset disposition of trough side walls 12,13 and depending skirts 16,17 enhances the structural stability of to the assembly, since this type of offset planar web or the like configuration in each instance contributes parallel reinforcement to the surrounding constructional environment in that location of the assembly which is operatively most important since it constitutes the portion of the clamp which is inserted into the anterior chamber of the eye.

At the same time, flat handles 3 and 7 in coextensive surface contact when the cover clamp part 6 is in extended position, provide an exterior temporary unitary laminate type association, similarly enhancing the structural stability of the external portion of the assembly which must undergo direct manual manipulation by the surgeon.

Accordingly, by the very advantageous nature of the positional disposition and related offset annular shape of the cover skirt and trough wall insertion portions, and of the analogous shape and orientation of the external handle portions, they are able to be efficiently formed as minimum dimension elements, both as to plate thickness and planar extent, to enable the lens forceps to be provided in a resultant composite cross sectional profile of minimum girth, and especially of optimal minimum linear dimension from the upper level of scoop 4 at medial and distal ends 18 and 19 to the level of the lowermost point or convex crest of scoop trough 5, so as to permit unfailingly the assembly to be removably inserted in a correspondingly optimal minimum linear size corneal incision for minimum trauma to the patient.

To this end, clamp parts 2 and 6 can be conveniently made from metal such as stainless steel or from inert plastic material by simple fabrication technique. In fact, due to the sturdy construction provided for such a small size assembly, as noted above, the lens forceps may be made inexpensively from appropriate metal or plastic material as a one-time use disposable unit, e.g. provided in sterile condition as a prepackaged commercial item.

The method of using the lens forceps assembly 1 according to the present invention may be seen from a study of FIG. 8. Preliminarily, by way of appropriate surgical procedure, the crystalline humor or eye lens L, normally located in the posterior chamber 30, distally of the vitreous body 31 containing the vitreous humor and medially of the iris 32, is surgically severed into two or preferably more lens portions or fragments. This may be done, for example, by inserting a loop-snare through an incision 33 in the cornea 34, after the lens L has been brought by the surgeon from the posterior chamber 30 into the anterior chamber 35 containing the aqueous humor, and then severing the lens L into two or more segments or fragments, as earlier described. Before insertion of the cutting instrument, the anterior chamber 35 may be deepened by injecting therein a viscoelastic substance such as Healon (a registered trademark), as noted more fully in said U.S. Pat. No. 4,538,611 to Kelman.

Upon removal o the loop-snare or other lens severing apparatus from the eye, the lens forceps 1 according to the present invention is inserted through the corneal incision 33, with the cover clamp part 6 in retracted position, so as to provide a free and open scoop 4 permitting easy manual manipulation for unhindered positioning of such a cut lens fragment L in trough 5. Thereafter, cover clamp part 6 is slid forward on scoop handle 3, guided by the depending skirts 16,17, until scoop cover 8 closes over scoop 4 and protrusions 10 on underside surface 7a of overlying handle 7 mesh with recesses 11 in upper side surface 3a of scoop handle 3, whereupon the closed assembly may be removed as a compact unit through the incision 33 in efficient manner without fear of the captively contained lens fragment L falling out of the enclosing cage 9.

It will be realized that the procedure might be such that the lens would first be cut into a small and large set of fragments, the cutting instrument then temporarily removed to permit insertion of the forceps assembly for removing the small fragment of the set, followed by the reinsertion of the cutting instrument to cut the remaining large fragment of the set into two further smaller fragments, each of which would then be successively removed by the forceps assembly in the above described manner.

On the other hand, to minimize trauma to the eye, it is usually more desirable to accomplish the cutting of the lens into several small size fragments during a single insertion of the cutting instrument, and then successively insert the forceps assembly for extracting in turn each of the cut fragments.

Hence, a method of using the lens forceps 1 is advantageously provided herein for extractive removal from the interior of an eye through a corneal incision of a surgically severed individual segmental lens portion or strip fragment located in the anterior chamber of the eye.

Such method comprises inserting the scoop of the scoop clamp part through the incision into the anterior chamber of the eye, i.e. with the cover clamp part in retracted position, and manipulating the inserted scoop sufficiently for spatially positioning the pertinent segmental lens portion therein with the corresponding peripheral edge portion of the lens portion in receiving disposition along the scoop trough, inserting the scoop cover of the cover clamp part through such incision sufficiently for manually controlled coactive stationary engagement of the overlay handle with the scoop handle exterior to the eye and corresponding positioning of the inserted scoop cover in overlying covering relation with the scoop, i.e. thereby placing the cover clamp part in extended position, for forming a confining cage in the anterior chamber for clamped captive retention of the lens portion therein, and finally removing simultaneously the scoop and scoop cover through the corneal incision while maintaining the scoop cover in overlying covering relation with the scoop and the overlay handle in coactive stationary engagement with the scoop handle.

In essence, therefore, a small size ophthalmic surgical instrument is provided by way of the structural aspects of the present invention, which is comprised of only two relatively movable parts, the first including an elongated handle portion having at one end thereof a crescent shaped or sickle shaped curved scoop portion, and the second also including an elongated handle portion having at one end thereof a plate like end portion adapted to cover the open part of the curved scoop portion of the first part when the two handle portions are attached or coaligned with each.

Significantly, the curved scoop portion of the first part is, in transverse cross section, provided in the configuration of a generally V-shaped trough which substantially corresponds to the shape of the peripheral edge of the portion of the natural lens to be supported therein for extractive removal from within the eye.

Hence, in use, after the natural lens has been severed within the eye into several lens segments, the sickle shaped end or scoop of the first part of the lens forceps assembly is inserted into the eye through the described small corneal incision. One of the severed lens segments is then manipulated to be positioned with its curved peripheral edge seated in the V-shaped trough of the first forceps part and the second forceps part is then inserted through the same small incision in the eye such that the plate-like end portion thereof is positioned over the lens segment for retaining the same between the curved portion and plate-like portion of the forceps assembly. The two forceps parts are then releasably connected together in such coactive retention position, i.e. with the lens segment retained captively therebetween, and the forceps assembly is then withdrawn from the interior of the eye through the incision.

As may be realized from the above manipulative steps, the clamp handles are conveniently of the same general size and shape, but in any case the scoop handle must provide a sufficient length, for stationarily guidably supporting the overlay handle thereon when the cover clamp part is in retracted position during insertion of the scoop of the scoop clamp part into the eye, as well as for slidably guidably supporting the cover clamp part during its full amplitude of movement to extended position, and at the same time both handles must provide sufficient area for the surgeon to grasp them adequately for manual manipulation of the clamp parts to carry out reliably and efficiently the underlying retrieval and extraction procedure, whereupon the cover clamp part may be again retracted when the assembly has been withdrawn from the eye.

It will be clear from the foregoing that the necessary access incision need only be as large as the chordal height of the cut lens segment of the natural lens, which is advantageously selected to be only a fraction of the size of the whole natural lens. In this regard, the sickle shaped or curved scoop portion preferably is generally semicircular in the direction of its length, has a generally V-shaped transverse cross section, especially with each wall of the V structure being approximately 1 mm in length, i.e. height, and the sickle shaped or crescent curved scoop portion having a radius of approximately 3 mm in length.

As a study of FIGS. 2 and 6 will show, the longitudinal scoop distance D is only important insofar as trough 5 must be able to accommodate a maximum chordal length of a cut lens segment, i.e. at most being equal to the diameter of the lens L. Since the longitudinal forceps assembly is intended for insertion crosswise of the cornea wall, this dimension D is not critical, as the incision will accommodate any appropriate length passing crosswise thereof (see FIG. 8).

On the other hand, to minimize the linear extent of the incision and in turn the trauma to the patient, the depth dimension X of the scoop should be as small as possible, so that it will fit through the smallest size incision consistent with good surgical procedure. This depends on the strip size of the cut segments or fragments, as that dimension X must approximate the strip size of the cut lens fragments in terms of the radial length increment R between the midpoint $P_C$ of the chord edge C of the cut strip segment L and a tangent point $P_T$ in tangent line E parallel to that chord C and located at the peripheral or opposing edge of strip segment L (see FIG. 6).

The forceps assembly significantly lends itself to dimensioning with comparatively shallow curved scoop configurations, permitting the surgeon to cut the lens into three or four generally parallel chord cut edge strip fragments, of decreasing chord length C from a maximum at a cut at or near the diameter of the lens corresponding to dimension D to a minimum chord length, e.g. corresponding to that portion of the chord line $C_G$ within scoop 4 at the outer or bottom crest area of its curved portion relative to the level of the medial and distal upper ends 18 and 19 thereof (see FIG. 6).

On the other hand, as to the height R of the cut segments, i.e. the vertical width from one cut chord edge C to the other E or from such a cut chord edge C to the periphery as E), this may readily correspond to the height dimension G, which for a 10 mm diameter lens would be approximately 3.3 mm if the lens is cut into three more or less equal width strips, or approximately 2.5 mm if the lens is cut into four such width strips. Clearly, the narrower the strip width R of the cut segments, the shallower the scoop need be, i.e. the dimension X.

Nevertheless, for an efficient retrieval operation, it is desirable that scoop 4 be fully open and unencumbered (see FIG. 4) so as to present a direct path into trough 5 for the particular fragment being extracted, without side encumbrances in the medial open area of scoop 4 between the overlying scoop cover 8 and the adjacent curved walls 12,13 of trough 5 therebelow. While this might otherwise permit dislodgement and loss laterally outwardly from trough 5 of an already retained fragment, after cover clamp part 6 has been extended to form the confining cage 9 and while the assembly is being withdrawn through the incision, should such fragment be of relatively short chordal length C and narrow strip width R, advantageously this is pointedly avoided by the coacting presence of the selectively sized upwardly directed side walls 12,13 and depending skirts 16,77.

Specifically, by appropriate selection of the trough side wall height $H_1$ and especially of the depending skirt height $H_2$ (since this latter dimension is less than the full height X and the skirts are remote from scoop 4 until after the sought segment or fragment has been negotiated into trough 5), the intervening gap distance G can be minimized and the threat of loss of an already captively retained segment laterally outwardly from the scoop can be overcome completely. Thus, if a segment L, having a strip width R corresponding to this vertical distance G, and resting in trough 5 such that its upper cut edge C is at the height of chord line $C_G$, were upwardly dislodged an increment corresponding to height $H_1$ during removal of the assembly through the incision, it would reach the depending skirt line S before its outer peripheral edge E would be raised sufficiently to clear the top edge of the adjacent portion of trough 5 thereat, i.e. at the height of trough line T.

To this end, several cover clamp parts 6, having skirts 16,17 of correspondingly increasing height $H_2$ from one to the next, may be provided for alternative individual use with scoop clamp part 2, in dependence upon the strip width R of the particular segment L being extracted.

Thus, the forceps assembly and method of use thereof are readily conformable to the underlying lens cutting surgical procedure, for enabling usage of the smallest possible incision in the cornea, and tailoring of the forceps to corresponding minimum scoop size consistent with the cutting procedure without fear of extraneously induced difficulties either in manipulating the cut lens segment into the scoop or in the loss thereof from the scoop during withdrawal of the assembly through the corneal incision.

It will be understood, of course, that any means may be employed to cut the lens into fragments, and that the assembly and conjoint method of use according to the present invention will effectively serve to retrieve and extract the individual cut segments or fragments, regardless of the manner in which they may have been preliminarily cut.

It will be appreciated that the foregoing specification and accompanying drawings are set forth by way of illustration and not limitation of the present invention, and that various modifications and changes may be made therein without departing from the spirit and scope of the present invention which is to be limited solely by the scope of the appended claims.

What is claimed is:

1. Lens forceps for extractive removal from the interior of an eye through a corneal incision of a surgically severed individual segmental lens portion, which comprises a manually manipulatable eye lens size clamp of two relatively longitudinally movable parts, including a longitudinal scoop clamp part having a scoop handle provided with a generally crescent shaped longitudinal scoop forwardly extending from the scoop handle and defining an upwardly open receiving trough of conforming size and shape to the corresponding perimetric profile of such a segmental lens portion for receiving such a lens portion therein, and a longitudinal cover clamp part having an overlay handle provided with a longitudinal scoop cover forwardly extending from the overlay handle, the scoop clamp part and cover clamp part being cooperatively arranged for manually controlled relative longitudinal movement therebetween an,, in one position of such movement, manually controlled removable coactive stationary engagement of the overlay handle with the scoop handle and corresponding positioning of the scoop cover in overlying covering relation with the scoop and forming therewith a confining cage for clamped captive retention of such a lens portion therein for permitting removal thereof from the eye through the corneal incision.

2. Forceps of claim 1 wherein releasable interlocking means are provided on the scoop clamp part and cover clamp part for maintaining such parts in interlocked stationary engagement and cage forming relation, when such parts are in said one position.

3. Forceps of claim 2 wherein the interlocking means include cooperating interlocking elements located correspondingly on the scoop handle and overlay handle.

4. Forceps of claim 3 wherein the interlocking elements include protrusions on one such handle and protrusion receiving locking recesses on the other such handle.

5. Forceps of claim 1 wherein the scoop trough is generally V-shaped in cross sectional profile.

6. Forceps of claim wherein guide means are provided for maintaining the scoop clamp part and cover clamp part in generally fixed transverse positional relation to each other while permitting relative longitudinal movement therebetween.

7. Forceps of claim 6 wherein the scoop trough has upwardly directed lateral side walls and the scoop cover has lateral side portions arranged for spaced overlying registry with the corresponding side walls of the trough when the scoop clamp part and cover clamp part are in said one position, and said guide means include downwardly depending lateral skirts provided on the scoop cover lateral side portions in facing spaced relation to the side walls of the trough when said parts are in said one position, and arranged for guidingly embracing the adjacent portions of the scoop handle during a portion of such relative longitudinal movement.

8. Forceps of claim 7 wherein the scoop has a longitudinal dimension generally corresponding to the diameter of an eye lens, and a depth dimension from the level of the scoop handle to the level of the lowermost portion of the scoop trough of less than the corresponding radius of the eye lens, and the scoop cover skirts and trough side walls are sized to provide a selective gap therebetween of a distance at most equal to about on fourth of the corresponding longitudinal dimension of the scoop when the scoop clamp part and cover clamp part are in said one position.

9. Method of using the lens forceps of claim 1 for extractive removal from the interior of an eye through a corneal incision of a surgically severed individual segmental lens portion located in the anterior chamber of the eye, which comprises inserting the scoop of the scoop clamp part through such incision into the anterior chamber of the eye and manipulating the inserted scoop sufficiently for spatially positioning such segmental lens portion therein with the corresponding peripheral edge portion of such lens portion in receiving disposition along the scoop trough, inserting the scoop cover of the cover clamp part through such incision sufficiently for manually controlled coactive stationary engagement of the overlay handle with the scoop handle exterior to the eye and corresponding positioning of the inserted scoop cover in overlying covering relation with the scoop for forming therewith a confining cage in the anterior chamber for clamped captive retention of the lens portion therein, and removing simultaneously the scoop and scoop cover through the corneal incision while maintaining the scoop cover in overlying covering relation with the scoop and the overlay handle in coactive stationary engagement with the scoop handle.

10. Lens forceps for extractive removal from the interior of an eye through a corneal incision of a surgically severed individual segmental lens portion, which comprises a manually manipulatable eye lens size clamp of two relatively longitudinally movable parts, including a longitudinal scoop clamp part having a scoop handle provided with a generally crescent shaped longitudinal scoop forwardly extending from the scoop handle and defining an upwardly open receiving trough of conforming size and shape to the corresponding perimetric profile of such a segmental lens portion for receiving such a lens portion therein and forwardly terminating in a forwardmost scoop tip, and a longitudinal cover clamp part having an overlay handle provided with a longitudinal scoop cover forwardly extending from the overlay handle and forwardly terminating in a forwardmost cover tip, the scoop clamp part and cover clamp part being cooperatively arranged for manually controlled relative longitudinal movement therebetween a first position in which the scoop cover does not overlie the scoop and a second position in which the scoop cover is in overlying covering relation with the scoop and forms therewith a confining cage for captive retention of such a lens portion therein for permitting removal thereof from the eye through the corneal incision, the scoop tip and cover tip in said second position of such longitudinal movement being in closely adjacent relation.

11. Forceps of claim 10 wherein releasable interlocking means are provided on the scoop clamp part and cover clamp part for maintaining such parts in interlocked stationary engagement and cage forming relation, when such parts are in said second position.

12. Method of using the lens forceps of claim 10 for extractive removal from the interior of an eye through a corneal incision of a surgically severed individual segmental lens portion located in the anterior chamber of the eye, which comprises inserting the scoop of the scoop clamp part through such incision into the anterior chamber of the eye and manipulating the inserted scoop sufficiently for spatially positioning such segmental lens portion therein with the corresponding peripheral edge portion of such lens portion in receiving disposition along the scoop trough, inserting the scoop cover of the cover clamp part through such incision sufficiently for manually controlled engagement of the overlay handle with the scoop handle exterior to the eye and corresponding positioning of the inserted scoop cover in overlying covering relation with the scoop for forming therewith a confining cage in the anterior chamber for captive retention of the lens portion therein, and such that the scoop tip and cover tip are maintained in closely adjacent relation, and removing simultaneously the scoop and scoop cover, with the lens portion captively retained therebetween, through the corneal incision while maintaining the scoop cover in overlying covering relation with the scoop and the overlay handle in engagement with the scoop handle.

* * * * *

UNITED STATES PATENT AND TRADEMARK OFFICE
CERTIFICATE OF CORRECTION

PATENT NO. : 4,791,924
DATED : December 20, 1988
INVENTOR(S) : CHARLES D. KELMAN It is certified that error appears in the above-identified patent and that said Letters Patent is hereby corrected as shown below:

Claim 1, line 54, delete "an,," and substitute therefor --and,--.

Claim 6, line 10, after "claim" insert --1--.

Claim 8, line 35, delete "on" and substitute therefor --one--.

Signed and Sealed this

Twentieth Day of June, 1989

Attest:

DONALD J. QUIGG

*Attesting Officer*    *Commissioner of Patents and Trademarks*